(12) United States Patent
Tinnefeld et al.

(10) Patent No.: US 10,099,195 B2
(45) Date of Patent: Oct. 16, 2018

(54) METHOD FOR POSITIONING STRUCTURES IN INDENTATIONS AND ARRANGEMENTS THUS OBTAINABLE

(71) Applicant: Technische Universitaet Braunschweig, Braunschweig (DE)

(72) Inventors: Philip Tinnefeld, Munich (DE); Guillermo Acuna, Braunschweig (DE); Enrico Pibiri, Braunschweig (DE)

(73) Assignee: Technische Universität Braunschweig, Braunschweig (DE)

( * ) Notice: Subject to any disclaimer, the term of this patent is extended or adjusted under 35 U.S.C. 154(b) by 407 days.

(21) Appl. No.: 14/687,999

(22) Filed: Apr. 16, 2015

(65) Prior Publication Data

US 2015/0298090 A1    Oct. 22, 2015

(30) Foreign Application Priority Data

Apr. 17, 2014  (DE) .................. 10 2014 105 488

(51) Int. Cl.
| | | |
|---|---|---|
| *C12Q 1/68* | (2018.01) | |
| *B01J 19/00* | (2006.01) | |
| *C12Q 1/6874* | (2018.01) | |
| *B82Y 20/00* | (2011.01) | |
| *B82Y 30/00* | (2011.01) | |

(52) U.S. Cl.
CPC ............ *B01J 19/0046* (2013.01); *C12Q 1/68* (2013.01); *C12Q 1/6874* (2013.01); *B01J 2219/00317* (2013.01); *B01J 2219/00576* (2013.01); *B01J 2219/00587* (2013.01); *B01J 2219/00596* (2013.01); *B01J 2219/00608* (2013.01); *B01J 2219/00612* (2013.01); *B01J 2219/00626* (2013.01); *B01J 2219/00637* (2013.01); *B01J 2219/00677* (2013.01); *B01J 2219/00722* (2013.01); *B82Y 20/00* (2013.01); *B82Y 30/00* (2013.01)

(58) Field of Classification Search
CPC ......... C12Q 1/68; C12M 1/00; B01J 19/0046; C40B 40/066
See application file for complete search history.

(56) References Cited

U.S. PATENT DOCUMENTS

2010/0009872 A1    1/2010  Eid et al.

FOREIGN PATENT DOCUMENTS

| | | |
|---|---|---|
| DE | 10 2012 107 718 A1 | 2/2014 |
| WO | 2011/031313 A2 | 9/2010 |

OTHER PUBLICATIONS

Heuke et al, Placing Individual Molecules in the Center of Nanoapertures, 2014, Nano Lett., 14, 391-395, publicly available on Jun. 6, 2013.*
Grohmann et al., "Making connections—strategies for single molecule fluorescence biophysics", Current Opinion in Chemical Biology, 2013, pp. 691-698, vol. 17.
Gietl et al., "DNA origami as biocompatible surface to match single-molecule and ensemble experiments", Nucleic Acids Research, 2012, p. e110, vol. 40, No. 14.
Pibiri et al., "Single-Molecule Positioning in Zeromode Waveguides by DNA Origami Nanoadapters", ACS Publications, Web.

\* cited by examiner

*Primary Examiner* — Narayan K Bhat
(74) *Attorney, Agent, or Firm* — W&C IP (57) ABSTRACT

Positioning structures in at least one indentation present on a or in a support, wherein said indentation is an indentation having a diameter in the nanometer range, makes it possible to position the structure in the indentation substantially centrally with defined orientation. A support having at least one indentation, wherein the indentation has a size in the nanometer range, includes a predetermined structure which is arranged substantially centrally within said indentation and which optionally has a functional unit diametrically opposite to the side pointing to the bottom surface. The arrangement is especially suitable for single molecule analysis and, here especially, for single molecule sequencing and other high-throughput methods.

11 Claims, 6 Drawing Sheets

METHOD FOR POSITIONING STRUCTURES IN INDENTATIONS AND ARRANGEMENTS THUS OBTAINABLE

FIELD OF THE INVENTION

In a first aspect, the present invention is directed to a method for positioning structures in at least one indentation present on a or in a support, wherein said indentation is an indentation having a diameter in the nanometer range. The method according to the invention makes it possible to position said structure in the indentation substantially centrally. In a further aspect, the present invention is directed to an arrangement of a support having at least one indentation, wherein this is one having a size in the nanometer range. The arrangement further comprises a predetermined structure which is arranged substantially centrally with defined orientation within said indentation and which optionally has a functional unit diametrically opposite to the side pointing to the bottom surface. Said arrangement according to the invention is especially suitable for single molecule analysis and, here especially, for single molecule sequencing and other high-throughput methods.

BACKGROUND

Single molecule techniques have a substantial influence on the developments in the nanobiotechnology field, such as super-resolution microscopy or single molecule DNA sequencing. In this connection, the difficulty is based less on the detection of single molecules, and more on the provision of techniques making it possible not to detect surrounding molecules. A successful approach for excluding such background molecules, i.e. molecules which are not to be detected, is the use of small wells or indentations, for example small wells or indentations in the nanometer range, formed in an approximately 100 nm thick metal layer situated on a glass support. Said wells or indentations having a diameter below approximately half the wavelength of visible light do not allow the diffusion of said light and are therefore referred to as zero-mode waveguides (ZMWs). Said zero-mode waveguides or ZMWs are also referred to as nanoapertures. In said ZMWs, evanescent light occurs near the glass support only to a slight extent, making it possible to observe single fluorescent molecules in biologically relevant concentrations in the nanomolar or micromolar range. These nanophotonic structures allow a breakthrough in single molecule real-time DNA sequencing and in investigating translation. To utilize the full potential of said nanophotonic structures, it is still necessary, however, to resolve various challenges. Firstly, single molecule techniques typically require exactly one molecule, such as a polymerase molecule for sequencing by means of ZMW. If there is more than one polymerase, this rapidly leads to dephasing, and so the sequence information is lost. Currently, said ZMWs or nanoapertures are loaded with a statistical Poisson distribution; this leads to a theoretical maximal distribution of single molecules in said ZMWs of approximately 37%. A second substantial challenge is the fluorescence of the single molecules within the ZMWs, i.e. having a signal as homogeneous as possible. This is not fully understood and most studies focus on FCS analysis, which is formed as an average via the total ZMW volume. A metal coating of the support to form the ZMW can, for example, lead to an altered (plasmon) excitation and the fluorescence process can be altered by quenching because of energy or electron transfer to the metal. Lastly, the radiation rate of the fluorophores may be altered. Furthermore, the radiation rate of the fluorophores may be intensified or reduced. A study which recently appeared showed that these processes are strongly position-dependent and the strongest fluorescence is obtained in nanoapertures having a diameter of 375 nm in the center thereof, Heucke S., et al., Nano Letters, 2014, 391 to 395.

US 2010/009872 describes methods for the targeted loading of biochips with single molecules. It describes DNA origami structures having single-stranded overhangs, to which functional units are coupled, being introduced into array structures. This represents the underlying prior art, specifically in which a distribution of a single structure is present in the ZMWs or nanoapertures with a Poisson distribution.

However, there is still a need to provide methods and arrangements which allow a targeted positioning of structures in the centers of the ZMWs or nanoapertures. More particularly, there is a need for methods and arrangements, where the loading with single molecules not only corresponds to the Poisson distribution, but is also present at a higher percentage in the single indentations or nanoapertures.

SUMMARY

In a first aspect, the present application provides a method for positioning structures in ZMWs or nanoapertures, i.e. in indentations, wherein said indentations have a diameter in the nanometer range of 300 nm and less. The method comprises the steps of providing a support having at least one indentation, wherein said indentation exhibits a diameter in the nanometer range of ≤300 nm. The bottom surface of the support that is exposed in the indentation is one which is preferably planar and permeable to light. On its exposed bottom surface, there is arranged a first binding partner. Furthermore, there is provided a structure which has a predetermined structure formed from nucleic acids. Said structure has on one side second binding partners which can form a binding pair with the first binding partner. The method according to the invention further comprises the step of introducing said structure into the at least one indentation and immobilizing said structure in the indentation via the binding partners with the formation of a binding pair between said first and second binding partners. The second binding partner is arranged on only one side of the structure in such a way that said structure is positioned substantially centrally in the indentation. This also makes a defined orientation of the structure in the indentation possible.

The structure is, for example, one based on a DNA origami. The expression "structure based on a DNA origami" is understood here to mean a DNA origami formed from a scaffold DNA strand and short DNA segments which form a predetermined structure of the scaffold DNA strand. Alternatively, the structure based on a DNA origami can also be constructed only from short DNA segments, as described in the literature, Wei B., et al., Nature, 485, 623 to 626, 2012.

The expression "DNA", as used here, is understood to mean not only strands of deoxyribonucleic acids, but also analogous structures, such as strands of ribonucleic acids, PNA, LNA, etc.

Unless otherwise stated, the word "or" is used in the inclusive sense of "and/or" and not in the exclusive sense of "either/or".

In the case of use of the expression "diameter", the shortest distance between two opposing sides is meant.

The expression "predetermined structure formed from nucleic acid molecules" refers to a two- or three-dimensional structure of predetermined shape. Said structure is formed at least in part from nucleic acid molecules. Preferably, said nucleic acid molecules are DNA molecules. In a particularly useful embodiment, the DNA molecules are self-assembling DNA structures obtained by the so-called DNA origami technique.

According to the invention, it was found that, by positioning the binding partner in the structure to be positioned in the indentation, it is possible to improve the prior art-described Poisson distribution of only one molecule structure in the indentations. Furthermore, it is possible to control the orientation of the structures in the indentations, i.e. a defined orientation of the structure in the indentation is possible. Functional units possibly present, which are preferably likewise arranged substantially centrally in the structure, then allow positioning of said functional units as centrally as possible in the indentations, such as the nanoapertures, in order thus to achieve the strongest fluorescence in the case of fluorescent dyes for example and to suppress possible quench effects in the edge region of said indentations. The spectroscopic properties are therefore more homogeneous than the randomly distributed structures in the indentations, as described in the prior art.

Using the structure having a predetermined structure formed from nucleic acid, such as a DNA origami, it is possible to form very precise structures of a particular dimension and, additionally, to position further functional units by means of suitable molecules which bind to said structure.

In one embodiment, the method is one in which the provided structure having a predetermined structure formed from nucleic acid is one which has at least two, such as three, four, five or more, second binding partners on one side of the structure and said at least two, three, four, five or more second binding partners are arranged around the center of the structure.

By means of the second binding partner defined in terms of its position, preferably arranged around the center of the structure, it is possible for said structure not to be immobilized in the indentation in such a way that it only partly covers the bottom surface and other parts stick out from the bottom surface at an angle, i.e. said structures are not transverse in the indentation. A problem which, in the prior art, has led to the fact that not only one structure is present in the indentation, but also multiple structures are bound in the indentation.

According to the invention, it is now specifically possible to occupy the indentations, i.e. the nanoapertures, with exactly one structure. By means of the appropriate arrangement of the second binding partners on said structure, it is possible for said structures to be immobilized in the indentations on the bottom surface, via formation of a binding pair with the first binding partner, in such a way that the structures or the functional units present on said structures are central in the indentation in order thus to maintain the homogeneity of the measurement signals obtained using said indentations in the form of nanoapertures.

Furthermore, the arrangement of the binding partners on only one side of the structure achieves a defined orientation of said structure in the indentation.

Furthermore, appropriate thermodynamic method steps can achieve the substantially central immobilization of the structures in the indentation. This means that the structure has more than one binding partner, such as at least three, four or more, and adjusting appropriate parameters, such as time and temperature, can control the immobilization via formation of the binding pairs, so that immobilization only occurs when all binding partners of the structure form a binding pair with a binding partner on the bottom surface of the indentation. If, for example in the case of four binding partners present on the structure, only one or two binding pairs are formed, said binding pairs are detached again at appropriately set temperature conditions, whereas the structure which forms binding pairs with all four binding partners remains immobilized on the bottom surface. This makes positioning including defined orientation possible.

The central positioning of the structure can also be achieved by having a gradient, i.e. an intensification of the interactions via formation of the binding pairs, of the second binding partners on the structure. For example, more potential second binding partners can be arranged more centrally than in the peripheral regions of the structure. This means that the strength of binding is higher in the case of central positioning of the structure in the indentation than in the case of a more peripheral arrangement or in the case of an incorrect orientation of the structure in the indentation.

In one embodiment, the ratio of the diameter of the structure to the diameter of the indentation or to the diameter of the bottom surface of said indentation is selected in such a way that said ratio is at least 0.5, such as at least 0.6, for example at least 0.7, such as at least 0.8. The ratio of said structures is selected in relation to the size of the indentation in such a way that a precise positioning of single structures is possible in said nanoapertures or ZMWs.

The binding partners present on the structure allow the precise positioning of the structure on the bottom surface of the indentation, with the structure and, here especially, the functional unit being appropriately aligned as centrally as possible.

As explained, the structures are preferably DNA origami structures. The second binding partner on said structure is formed in such a way that it has a segment which can form a binding pair with the further binding partner present on the bottom surface of the indentation. A further segment of said second binding partner can be a structure having complementary nucleic acid segments, complementary to nucleic acid segments in the stated structure, such as the DNA origami. In the event of appropriate hybridization of said DNA segments to the complementary DNA segments on the structure, the corresponding binding partners can therefore be positioned at predetermined positions. By means of this positioning, it is possible for said structure, which has a predetermined structure formed from nucleic acid, to be immobilized in the indentation only with very limited possibilities, specifically only in such a way that only one structure is immobilized in the indentation and not two structures. Furthermore, said structure allows an appropriate predetermined, substantially central arrangement of functional units present on a corresponding structure. Positioning the binding partners on the structure makes a defined orientation of said structure in the indentation possible.

In one embodiment, the indentation is a nanoaperture or a ZMW. According to the invention, a method is therefore provided for immobilizing said structures, which have a predetermined structure formed from nucleic acid, in the nanoapertures, with the percentage of nanoapertures having exactly one immobilized structure being above that of the Poisson distribution.

In one embodiment, the side having the second binding partner of the structure and the bottom surface of the support that is exposed in the indentation are positioned substantially parallel to one another. In this case, said side of the structure can be flattened. In one embodiment, said structure based on a nucleic acid structure is disk-shaped, for example as a DNA origami.

The binding partners used can be known binding partners. Said binding partners allow the formation of a binding pair via covalent or noncovalent bonding. In one embodiment, one binding partner is biotin and the other binding partner is an avidin or avidin derivative, for example neutravidin and streptavidin. Other possible binding partners are complementary nucleic acid strands, i.e. binding takes place via appropriate hybridization of these complementary strands. Further possibilities include known ligand receptor binding partners, antibody/antigen binding partners, covalent coupling partners (to the amino groups with NHS esters, thiols with maleimides, etc.) and also click reaction partners.

In one embodiment, the structure is one which has a functional unit bound to said structure. Appropriate binding of said functional unit can be effected covalently or noncovalently, for example by hybridization of complementary nucleic acid strands. In one embodiment, said functional unit comprises a functional segment and a segment allowing the binding to the structure via a noncovalent or covalent bond, for example a nucleic acid sequence complementary to a nucleic acid sequence present in the structure and having a predetermined position. By means of the positions, known in the structure, of the individual constituents, more particularly the nucleic acid molecules, it is possible to position the functional units, as well as the binding partners, at predetermined positions. In one embodiment, the functional unit is positioned in such a way that it is substantially central in the indentation. Said functional unit is diametrically opposite to the side having the second binding partner.

The following may be mentioned as functional segments of said functional units: a biomolecule, a dye, enzyme, protein, nanoparticle, antibody, DNA structure, quantum dot, etc. The appropriate functional segments in the functional unit are selected depending on the use.

The method according to the invention therefore involves immobilizing single structures on the bottom surface of said indentation, which can be a nanoaperture, in such a way that exactly one such structure, and not none or two, is present per indentation. More particularly, the structure is selected in such a way that, because of the size exclusion, only one structure, for example in the form of a DNA origami, fits into the indentation, and so there is an improved occupancy of said indentations with exactly one structure and, accordingly, assays can be carried out with a higher yield. The size of said structure based on a nucleic acid structure is selected in accordance with the size of the indentation.

Alternatively or additionally, the number of binding partners present on the structure can be selected such that said structure is only immobilized by formation of binding pairs when a multiplicity, such as all binding partners of the structure form a binding pair with a binding partner on the bottom surface of the indentation.

The indentation is typically a substantially round indentation. However, other types of indentations are also possible, for example angular structures or semicircular or crescent structures. The structure is selected in such a way that, for example by means of size exclusion, an occupancy of said indentation by more than one molecule is ruled out. The presence of the second binding partner on only one side of said structure additionally ensures that the orientation of said structure in the indentation is controlled. Positioning said binding partners as centrally as possible on the structure additionally ensures that said structure is not immobilized in such a way, or in a number of more than one in the indentation, that the structure and, here too, the functional unit present is localized on the edge. Appropriate immobilization of said structure on the bottom surface of the indentation can therefore only substantially take place in one embodiment when said structure is substantially parallel to the bottom surface or when sufficient binding pairs are formed between the binding partners at a predefined temperature or other parameter. This also ensures that functional units are positioned at appropriately predetermined positions, specifically in such a way that they are present on the opposite side of the binding partners. Appropriate positioning is explained in detail with reference to the figures.

In terms of their size, the structures are selected such that they fit into the indentations, with said structures being selected in terms of their size such that not more than one thereof is immobilized on the bottom surface.

The expression "immobilized" is understood here to mean that the structure remains substantially unaltered at its position over the entire use. The immobilization can by all means be formed such that, under certain conditions, the structure can be detached from the bottom surface by breaking the binding pair in order to optionally immobilize there another structure.

In a further aspect, an arrangement is provided here. Said arrangement according to the invention is one having support having at least one indentation having a diameter in the nanometer range of ≤300 nm, wherein a first binding partner is arranged on the bottom surface of the support that is exposed in the indentation. In one embodiment, the support is permeable to light and the bottom surface is substantially planar. In said indentation, a structure is positioned on the bottom surface. Said structure comprises a predetermined structure formed from nucleic acid. In one embodiment, said structure is a DNA origami. On one side of said structure, there is a second binding partner. Said second binding partner forms a binding pair with the first binding partner in order to position and to immobilize said structure on the bottom surface of the indentation. The structure additionally has a functional unit on the diametrically opposite side having the second binding partner. In one embodiment, said functional unit present on the structure is arranged substantially in the center of the indentation.

The expression "substantially in the center" or the expression "substantially central", which are used here synonymously, is understood to mean that said structure is at a distance of at least 5 nm, such as at least 10 nm, from the edge regions. The central unit is at a distance from the edge to ensure that the function of a functional unit present (such as a polymerase) is not impaired, and to prevent a minimum distance in relation to a strong fluorescence quenching.

In one embodiment, the arrangement according to the invention is one wherein the structure present in the indentation is a predetermined structure formed from nucleic acid, such as a DNA origami. The ratio of the diameter of said structure or the ratio of covered area of said structure with respect to the area of the bottom surface is, for example, at least 0.5, such as 0.6, for example 0.7, such as at least 0.8.

In one embodiment, the arrangement according to the invention is obtainable using the method according to the invention.

Such arrangements according to the invention can be provided as biochips for example.

Said arrangements according to the invention can be utilized in various applications. For example, one use thereof concerns single molecule analysis, such as single molecule sequencing. According to the invention, it is possible to position, for example, one polymerase or another suitable enzyme per indentation in order to allow single molecule sequencing, such as, for example, single DNA sequencing.

Such arrangements are used especially in bioassays, such as in high-throughput analysis. Bioassays include binding of antibodies to an antigen (or of the analyte to be detected). This likewise includes enzyme assays with immobilized enzymes, for example for screening of active ingredients.

DESCRIPTION OF THE DRAWINGS

The invention will be further explained with reference to the figures.

DETAILED DESCRIPTION

Figure 1A:
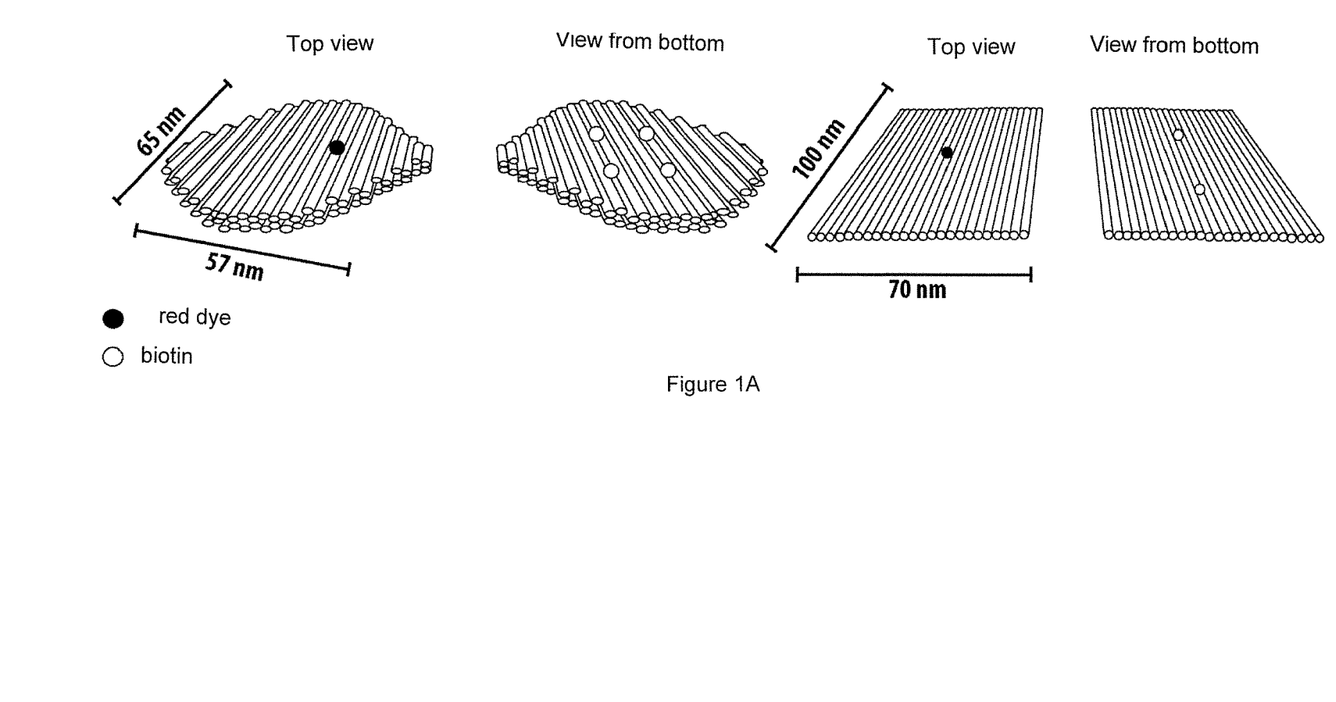
FIG. 1A shows the upper side and lower side of a structure which is positioned according to the invention in the indentation.

With reference to FIG. 1A, a dye, for example, is arranged on the upper side. It is also possible to arrange an enzyme, etc. Four or two biotins are arranged on the lower side. These biotin molecules are arranged around the center of the structure. The structure here is a disk-shaped DNA origami structure (left-hand side of FIG. 1A). The right-hand side of FIG. 1A shows a rectangular DNA origami structure, with a dye to be found on the upper side thereof and two biotin molecules to be found on the lower side thereof.

Figure 1B:
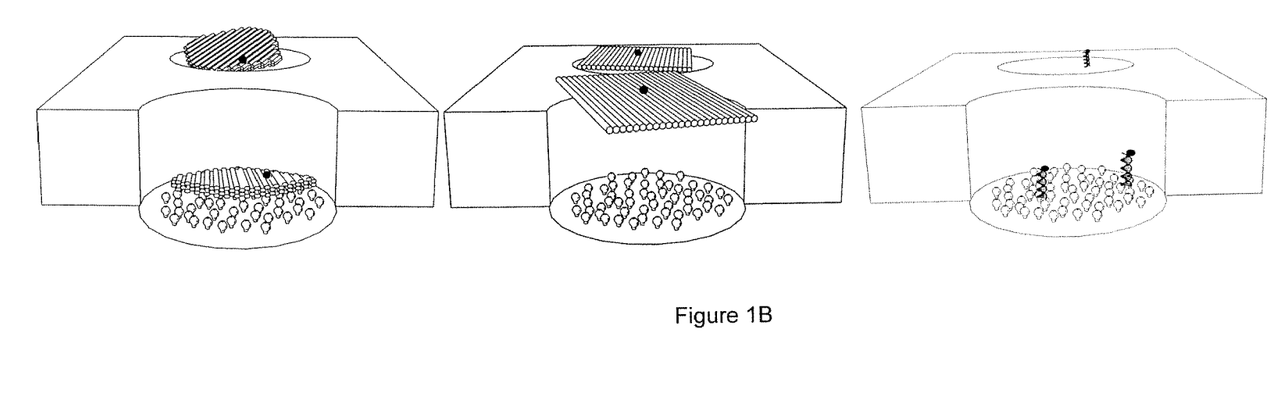
FIG. 1B shows DNA origami fit and non fit examples with respect to the indentation, and an example of the first binding partners for the DNA origami.

FIG. 1B shows how the disk-shaped DNA origami fits into the indentation, whereas the rectangular origami does not fit into the indentation because of its size and thus a steric hinderance or because of the size exclusion. The right-hand schematic in FIG. 1B, the cut-out, shows the first binding partners, neutravidin in this case. It can seen that they are randomly distributed on the bottom surface of the indentation.

Figure 1C:
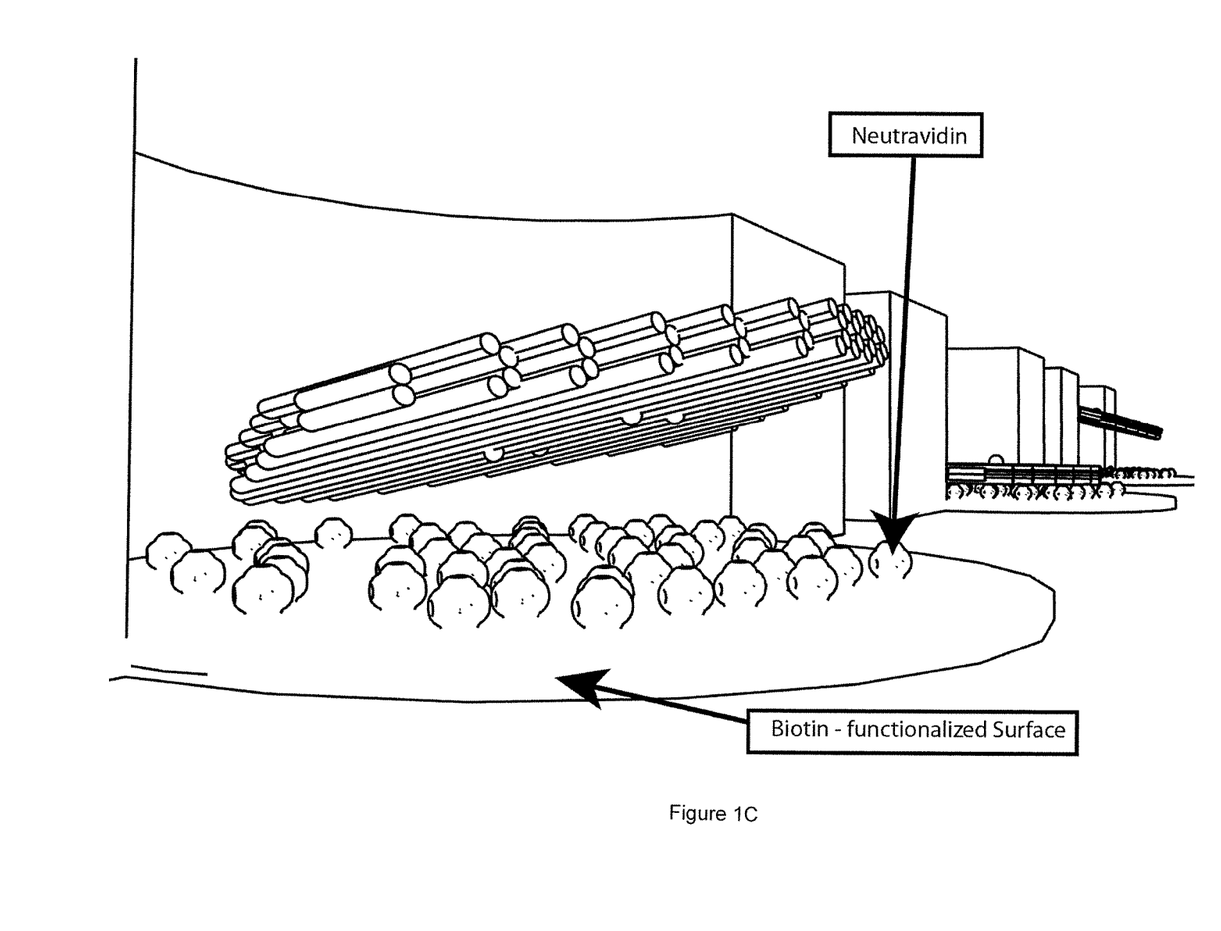
FIG. 1C shows the immobilization of the DNA origami structure.

FIG. 1C shows the immobilization of the DNA origami structure via the biotins as second binding partners to the neutravidins as first binding partners on the bottom surface of the indentation. Because of the positioning of the biotins on the structure, the structure is positioned substantially in the center of the indentation and thus the dye is positioned substantially in the center of the indentation.

Because of the size ratios of the structure to be immobilized and the indentation, it is possible in each case for only one of said structures to be present per indentation. Because of this appropriate selection of the parameters of the structure, it is possible to increase the proportion of indentations having exactly one positioned structure above the Poisson distribution.

Positioning the functional unit centrally in the indentation means that there is a distance to the sides of said indentation of at least 5 nm, such as at least 10 nm, for example at least 15 nm. The functional unit has a functional segment which can be a biochemical or chemical group, such as an enzyme, a binding group, more particularly a ligand, a receptor, an antibody, etc. The biochemical or chemical group is a group which allows processing or binding of a compound in order, for example, to emit electromagnetic waves, such as a chromophore or a fluorophore. In the case of DNA sequencing, the biochemical unit is the DNA polymerase, whereas the compound emitting electromagnetic waves, such as fluorescence, is a labeled nucleotide, more particularly a labeled nucleotide labeled with a fluorophore.

In another embodiment, the biological group can be a ligand or a receptor and the compound which can emit electromagnetic waves can be a labeled chemical compound or a biomolecule, for example a small molecule, the binding activity or binding affinity of which to said ligand or receptor is to be determined.

Positioning of the functional unit but also the binding partners in the structure can be carried out according to known methods. A person skilled in the art is aware of appropriate methods, especially for site-specific positioning in the case of molecules comprising nucleic acid sequences. Here, positioning can be effected biochemically or chemically. For example, positioning can be effected using reactive groups, such as a thiol group, NHS esters, amino groups, etc. Alternatively, positioning can be effected by means of single-stranded nucleic acid sequences which allow hybridization to predetermined segments of nucleic acid molecules in the structure.

The present arrangements can be used especially in DNA sequencing as well as in active ingredient development. They represent a platform for single molecule lab-on-a-chip, which allows parallel analyses of enzyme reactions, binding assays and active ingredient screening assays in a limited volume. The arrangements obtained using the method according to the invention, such as the nanoapertures, ZMWs, thus obtained, can achieve more homogeneous measurements, since disruptive effects owing to measurements in edge regions are avoided. In addition, the nanoapertures can be equipped to a greater extent with single structures.

The invention will now be more particularly elucidated on the basis of examples without being restricted thereto.

Example

A DNA origami disk and a rectangular DNA origami structure were prepared. Modified double-stranded DNA (dsDNA) for the stochastic immobilization was prepared as described in Heucke S., et al., Nano Letters 2014, 391-395. To compare the fluorescence of dyes in the case of dsDNA with that of DNA origami, reference measurements were carried out on glass supports (LabTek chambers, borosilicate, coverglass, 8 indentations, Thermo Scientific New, 155411).

The measurement of the fluorescence intensity distribution and the lifetime of the dsDNA and of the DNA origami disk was carried out using the dye ATTO647N and showed that both have a similar lifetime and intensity distribution (data not shown).

Determining the Positioning of the Dyes in the Indentations

Figure 2A:
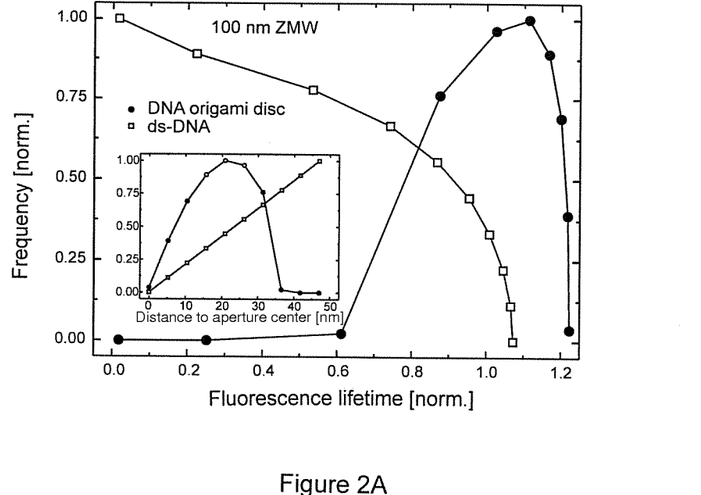
FIGS. 2A and 2B are graphs of Monte Carlo simulations.
Figure 2B:
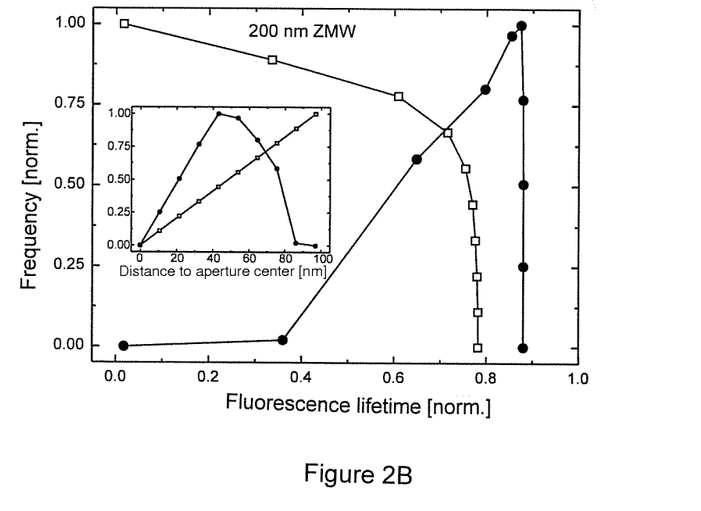

Monte Carlo simulations (FIGS. 2A-B) show that the distribution of the functional units immobilized via the structure is fundamentally different to randomly immobilized molecules (dsDNA). The functional units are situated close to the center of the structure, whereas randomly immobilized molecules have the greatest probability of becoming immobilized close to the nanoaperture wall.

Size-Exclusion Positioning of DNA Structures

Figure 3A:
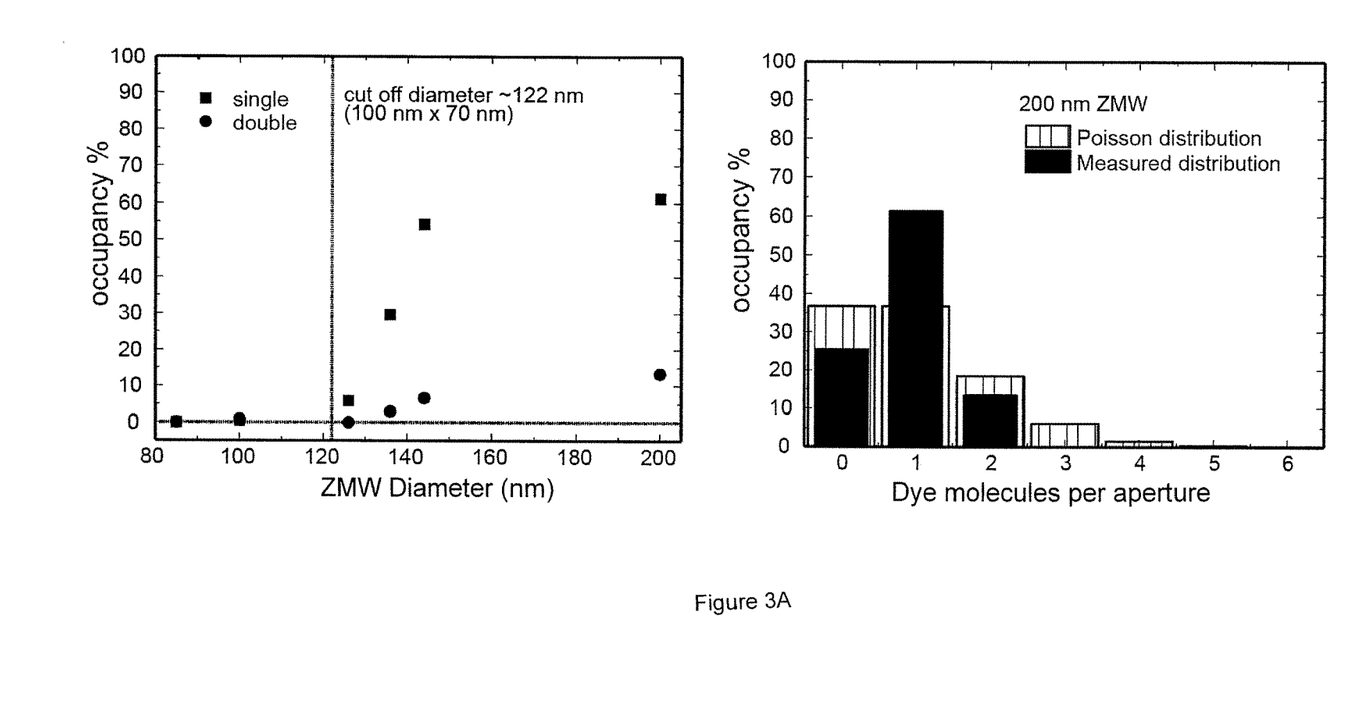
FIG. 3A line and bar graph results for size exclusion experiments with a rectangular DNA origami.

The DNA origami adapter used was a rectangular DNA origami measuring 100×70 nm. Single DNA strands were modified such that a red dye (ATTO 647N) is situated on the upper side and 2 biotins are situated on the lower side. The ZMWs were incubated for 30 min with neutravidin in MOPS (50 mM MOPS, 75 mM KOAc and 12.5 mM MgOAc, pH 7) buffer (1 mg/ml), washed 5 times with buffer solution and then incubated with a 45 nm DNA origami solution for 30 min. To remove nonbinding DNA origamis, the ZMW was washed 5 times with the buffer. To determine the occupancy, confocal recordings were carried out and the number of occupied ZMWs counted. After each scan, each occupied ZMW was run into the laser focus and the number of molecules determined through the bleaching steps in the time track recorded; see FIG. 3A.

Figure 3B:
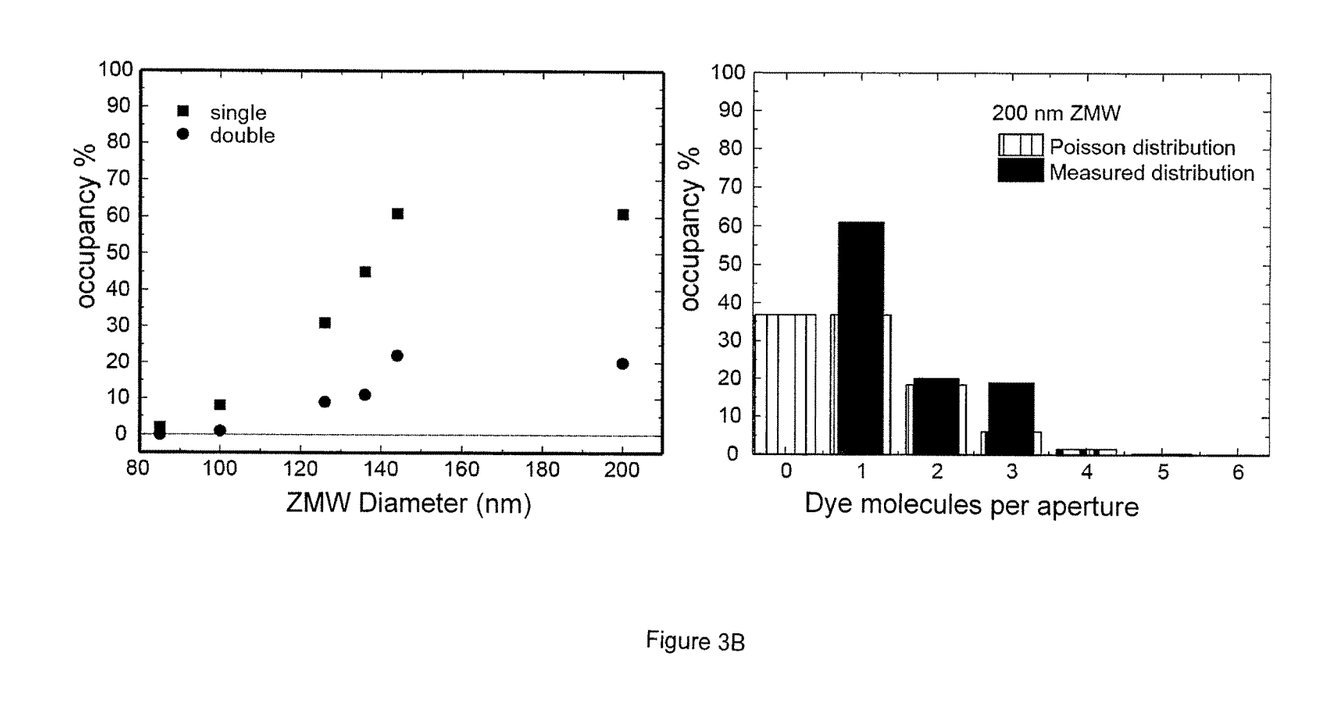
FIG. 3B line and bar graph results for size exclusion experiments with a rectangular DNA origami.

As can be seen in FIG. 3B, a correctly selected ratio of the diameter of the nanoaperture to the diameter of the structure which has a predetermined structure formed from nucleic acid, in this case a DNA origami disk, leads to an occupancy of exactly one structure per indentation that is above the Poisson distribution.

The nanoapertures (ZMWs) used were those from Pacific Bio Sciences, USA. These array chips were applied to conventional microscope slides. Each of said chips provided six different ZMW diameters in the range from 85 to 200 nm. The bottom surface of the indentation was functionalized with PEG-biotin in order to allow the immobilization of neutravidin. Nonspecific binding to the aluminum surface was passivated by phosphonates. Subsequently, neutravidin was bound to the biotin in order to provide appropriate arrays for investigating the binding of the structures.

Confocal Measurement and Analysis

All measurements were carried out using a homemade confocal setup based on an inverted microscope (IX71, Olympus) and an oil immersion objective (100×/NA 1.40, UPLSAPO100XO, Olympus). The dye used was the dye ATTO647N; this was excited at 640 nm with an 80 MHz pulsed laser diode, LDH-D-C-640, Picoquant, 20 µW. The polarization of the excited light was converted to circularly polarized light using a λ/4-plate (AQWP05M-600, Thorlabs). The ZMWs containing the immobilized DNA origamis were positioned into the laser focus using a Piezo stage (P-517.3CL, Physik Instrumente). After each scan, the molecules were selected and automatically positioned into the laser focus. The fluorescent light was collected by the same objective and focused through a 50 µm pinhole (Linos). The detection was carried out after a spectral filter (ET 700/75m, AHF and RazorEdge LP 647, Semrock) by an avalanche photodiode (τ-SPAD 100, Picoquant) and a PC board (SPC-830, Becker&Hickl).

The invention claimed is:

1. Arrangement having a support having at least one indentation having a diameter in nanometers range of ≤300 nm, wherein a first binding partner is arranged on a bottom surface of the support that is exposed in the indentation, and a structure positioned in said indentation, wherein said structure comprises a predetermined structure formed from nucleic acid, and the structure has on one side a second binding partner which has formed a binding pair with the first binding partner, wherein in the case of the structure, a functional unit is arranged on a diametrically opposite side to the one side having the second binding partner, wherein the second binding partner is arranged on only the one side of the structure in such a way that said structure is positioned substantially centrally in the indentation.

2. The arrangement according to claim 1, wherein the structure present in the indentation is the predetermined structure formed from nucleic acid and the ratio of a diameter of said structure to the diameter of the at least one indentation is at least 0.7.

3. The arrangement according to claim 1, wherein the structure present in the indentation is the predetermined structure formed from nucleic acid and the ratio of a diameter of said structure to the diameter of the at least one indentation is at least 0.8.

4. The arrangement according to claim 1, obtained by
providing the support having the at least one indentation having the size in the nanometers range of ≤300 nm, wherein the first binding partner is arranged on the bottom surface which is exposed as a result of the indentation on the support and which is planar and permeable to light,
providing the structure having the predetermined structure formed from nucleic acid, the structure has on one side the second binding partner which can form a binding pair with the first binding partner,
introducing the structure into the at least one indentation and immobilizing the structure in the indentation via the first binding partner and the second binding partner forming a binding pair,
wherein the second binding partner is arranged on only one side of the structure in such a way that said structure is positioned substantially centrally in the indentation.

5. The arrangement according to claim 1, wherein said arrangement is a biochip.

6. A method for using the arrangement of claim 1, comprising using the arrangement for one or more of single molecule analysis or bioassays.

7. The method of claim 6 wherein said using step is used for single molecule analysis and said single molecule analysis includes single molecule sequencing.

8. The method of claim 6 wherein said using step is used for bioassays which are configured for high-throughput analysis.

9. The arrangement according to claim 1 wherein the binding pair is covalent or noncovalent.

10. The arrangement according to claim 1 wherein one binding partner of said first and second binding partners is biotin.

11. The arrangement according to claim 1 wherein the functional unit is selected from the group consisting of a biomolecule, a dye, enzyme, protein nanoparticle, antibody, DNA structure, and quantum dot.

* * * * *